(12) United States Patent
Edgett et al.

(10) Patent No.: US 11,540,955 B2
(45) Date of Patent: *Jan. 3, 2023

(54) TAMPON ASSEMBLY HAVING A SHAPED PLEDGET

(71) Applicant: Edgewell Personal Care Brands, LLC, Chesterfield, MO (US)

(72) Inventors: Keith Edgett, Middletown, DE (US); Patrick Gorham, Wyoming, DE (US); George Jarmon, Camden/Wyoming, DE (US); Jessica LeMay, Portland, OR (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 733 days.

This patent is subject to a terminal disclaimer.

(21) Appl. No.: 16/504,547

(22) Filed: Jul. 8, 2019

(65) Prior Publication Data

US 2019/0328583 A1 Oct. 31, 2019

Related U.S. Application Data

(63) Continuation of application No. 15/399,108, filed on Jan. 5, 2017, now Pat. No. 10,383,776, which is a continuation of application No. 15/398,298, filed on Jan. 4, 2017, now Pat. No. 10,105,267, which is a continuation of application No. 14/807,163, filed on Jul. 23, 2015, now Pat. No. 10,105,266, which is a
(Continued)

(51) Int. Cl.
*A61F 13/20* (2006.01)
*A61F 13/28* (2006.01)
*A61F 13/34* (2006.01)
*A61F 13/26* (2006.01)
*A61F 13/15* (2006.01)

(52) U.S. Cl.
CPC ........ *A61F 13/2054* (2013.01); *A61F 13/202* (2013.01); *A61F 13/208* (2013.01); *A61F 13/2022* (2013.01); *A61F 13/266* (2013.01); *A61F 13/28* (2013.01); *A61F 13/34* (2013.01); *A61F 13/20* (2013.01); *A61F 13/26* (2013.01); *A61F 2013/15365* (2013.01); *A61F 2013/15422* (2013.01)

(58) Field of Classification Search
CPC ................ A61F 13/2054; A61F 13/202; A61F 13/2022; A61F 13/208; A61F 13/266; A61F 13/28; A61F 13/34; A61F 13/26; A61F 13/20; A61F 2013/15365; A61F 2013/15422
USPC ........................... 604/14, 15, 385.17, 385.18
See application file for complete search history.

(56) References Cited

U.S. PATENT DOCUMENTS

| | | |
|---|---|---|
| 3,320,956 A | 5/1967 | Steiger |
| 3,409,011 A | 11/1968 | Mittag |

(Continued)

*Primary Examiner* — Jacqueline F Stephens

(57) ABSTRACT

A tampon assembly having a barrel, a plunger, and a pledget is provided. The plunger is slidably received in the barrel. The pledget is in the barrel between the insertion tip and the plunger so that a force applied on the plunger can expel the pledget from the barrel. The barrel has a plurality of petals defining an insertion tip, which has a first taper ratio of more than about 0.3 to less than 1.0. The pledget has a shaped tip that is disposed in the insertion tip.

20 Claims, 4 Drawing Sheets

Related U.S. Application Data continuation of application No. 11/713,974, filed on Mar. 5, 2007, now Pat. No. 9,192,522, which is a continuation-in-part of application No. 10/834,386, filed on Apr. 28, 2004, now Pat. No. 8,197,434.

(60) Provisional application No. 60/467,482, filed on May 2, 2003.

(56) References Cited

U.S. PATENT DOCUMENTS

| | | | |
|---|---|---|---|
| 3,674,026 A | 7/1972 | Werner et al. | |
| 3,699,962 A | 10/1972 | Hanke | |
| 3,805,786 A | 4/1974 | Bernardin et al. | |
| 4,857,044 A | 8/1989 | Lennon | |
| 4,973,302 A | 11/1990 | Armour et al. | |
| 5,389,067 A | 2/1995 | Rejai | |
| 6,019,744 A | 2/2000 | Altdorf et al. | |
| 6,315,763 B1 | 11/2001 | Albright et al. | |
| 9,192,522 B2 * | 11/2015 | Edgett | A61F 13/202 |
| 10,383,776 B2 * | 8/2019 | Edgett | A61F 13/208 |
| 2003/0236499 A1 | 12/2003 | Fedyk et al. | |

* cited by examiner

TAMPON ASSEMBLY HAVING A SHAPED PLEDGET

CROSS-REFERENCE TO RELATED APPLICATIONS

This is a continuation application of copending U.S. patent application Ser. No. 15/399,108, filed Jan. 5, 2017, which is a continuation of U.S. patent application Ser. No. 15/398,298, filed Jan. 4, 2017, now U.S. Pat. No. 10,105,267, granted on Oct. 23, 2018, which is a continuation of U.S. patent application Ser. No. 14/807,163, filed on Jul. 23, 2015, now U.S. Pat. No. 10,105,266, granted on Oct. 23, 2018, which is a continuation of U.S. patent application Ser. No. 11/713,974, filed on Mar. 5, 2007, now U.S. Pat. No. 9,192,522, granted on Nov. 24, 2015, which is a continuation-in-part of U.S. patent application Ser. No. 10/834,386, filed on Apr. 28, 2004, now U.S. Pat. No. 8,197,434, granted on Jun. 12, 2012, which claims the benefit of U.S. Provisional Patent Application Ser. No. 60/467,482, filed May 2, 2003 the contents each being incorporated by reference herein in their entirety.

BACKGROUND OF THE INVENTION

1. Field of the Invention

The present invention is related to a tampon assembly. More particularly, the present invention is related to a tampon assembly that has a shaped pledget.

2. Description of Related Art

A tampon assembly is used to inject an absorbent or hygienic material, known as a tampon pledget, into the vaginal vault. The pledget of commercial tampon assemblies is typically positioned in a barrel for expulsion from a barrel by a plunger. The use of such assemblies requires a user to insert an end of the barrel into the vaginal vault.

Once the barrel has been inserted, the plunger can be used to expel the pledget from the end of the barrel into the vaginal vault. Once the pledget is in position, the pledget expands upon contact with moisture to conform to contours of the body and, thus, provide leakage protection Comfort to the user during insertion of the barrel and expulsion of the pledget is an important aspect for the commercial success of the tampon assembly. Furthermore, perceived and actual level of performance is also dependent how comfortable the applicator is to insert into the user's body.

Many attempts have been made to increase the comfort associated with the use of tampon assemblies. For example, the barrel of some tampon assemblies include a dome shaped end. The dome shaped end includes a number or plurality of shaped petals configured to open during expulsion of the pledget. Unfortunately, the petals themselves can be a source of discomfort. For example, the petals can collapse during insertion of the barrel, which can increase the force required to eject the pledget from the barrel. This has led prior assemblies to increase the thickness of the petals to prevent the petals from collapsing. However, the increased petal thickness can also increase the force required to eject the pledget from the barrel. Since increases in ejection force can result in the applicator being difficult to use, neither solution has been desirable.

Additionally, in prior assemblies having blunt or unshaped pledgets, users often push the pledget as far into the applicator tip as possible prior to insertion of the applicator. However, this can cause the petals to open prematurely, namely before insertion of the barrel into the body. The open petals provide prior barrels with a "claw-like" insertion tip, which can scratch during insertion of the barrel. Also, the open petals can close during the insertion process, which can pinch the skin of the user.

Accordingly, there is a continuing need for tampon assemblies that can increase comfort by addressing one or more of the aforementioned drawbacks and deficiencies.

BRIEF SUMMARY OF THE INVENTION

It is an object of the present invention to provide a tampon assembly having a shaped pledget.

It is another object to provide a tampon assembly having a tapered insertion tip that has some portion of its inside surface supported by a shaped pledget.

It is yet another object to provide a tampon assembly that has an applicator barrel that is easy to insert, and a shaped pledget that gradually opens the petals of the barrel.

These and other objects and benefits of the present invention are provided by a tampon assembly having a barrel, a plunger, and a pledget. The plunger is slidably received in the barrel. The pledget is in the barrel between the insertion tip and the plunger so that a force applied on the plunger can expel the pledget from the barrel. The barrel has a plurality of petals defining an insertion tip, which has a first taper ratio of more than about 0.3 to less than 1.0. The pledget has a shaped tip that is disposed in the insertion tip.

These and other objects of the present invention are also provided by a tampon assembly having a barrel, a plunger, and a pledget. The barrel has a plurality of petals defining an insertion tip. The insertion tip has an inner surface area. The plunger is slidably received in the barrel. The pledget has a shaped tip. The pledget is in the barrel so that the shaped tip supports a portion of the inner surface area. A force applied to the plunger can expel the pledget from the barrel through the plurality of petals.

The above-described and other features and advantages of the present invention will be appreciated and understood by those skilled in the art from the following detailed description, and drawings.

DETAILED DESCRIPTION OF THE INVENTION

Figure 1:
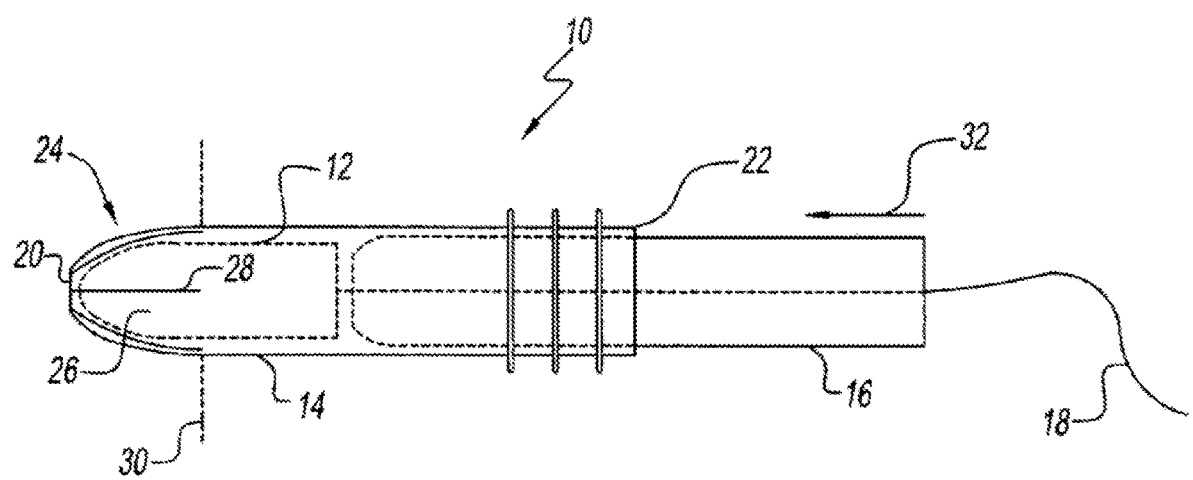
FIG. 1 is a side view of an exemplary embodiment of a tampon assembly according to the present invention.
Figure 2:
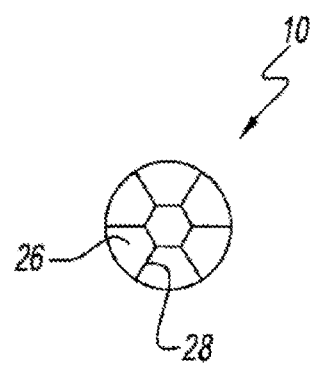
FIG. 2 is an end view of the assembly of FIG. 1.

Referring now to the drawings and more particularly to FIGS. 1 and 2, an exemplary embodiment of a tampon assembly generally represented by reference numeral 10 is illustrated. Assembly 10 has a shaped pledget 12, a barrel 14, and a plunger 16. Pledget 12 can include a withdrawal cord 18 connected thereto, which extends out of assembly 10.

Shaped pledget 12 is disposed in barrel 14 and significantly improves the performance of assembly 10 as compared to prior assemblies having a blunt or squared-off pledget.

Barrel 14 has a first end 20 and a second end 22. First end 20 defines an insertion tip 24 having a number or a plurality of petals 26. Petals 26 are defined in first end 20 by a number or plurality of slits 28. The number of slits 28 typically corresponds to the number of petals 26 present. Insertion tip 24 terminates at a plane 30 defined at the base or root of petals 26 (e.g., the bottom of slits 28).

Barrel 14 is illustrated by way of example as including six petals 26. Of course, it is contemplated by the present invention for barrel 14 to have more or less than six petals. For example, barrel 14 can have between about two to about eight petals 26. Base 43 of petals 26 may have hinges to pivot each of petals 26 into or out of barrel 14 along each hinge.

Plunger 16 is useable to expel pledget 12 from barrel 14. Plunger 16 is slidably disposed in barrel 14 at second end 22. Pledget 12 is expelled through first end 20 through the movement of plunger 16 in the direction of arrow 32. As plunger 16 moves in the direction of arrow 32, the plunger can urge pledget 12 into petals 26 until the petals open along slits 28 and the pledget is expelled from barrel 14 through insertion tip 24.

Figure 3:
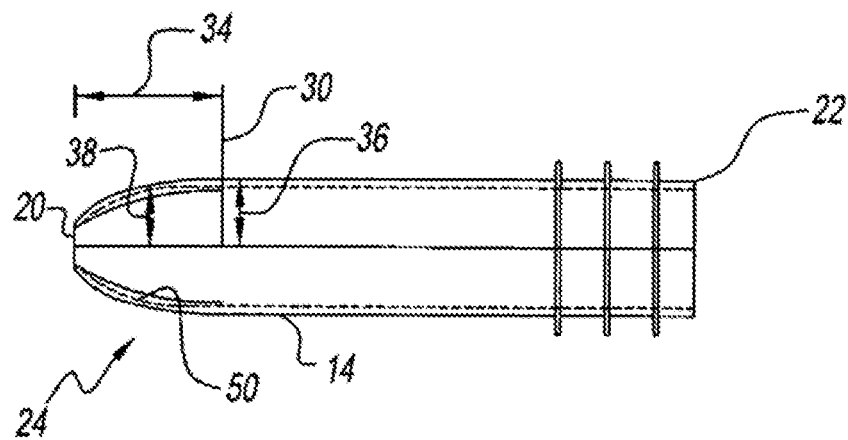
FIG. 3 is a side view of the barrel of FIG. 1.

Referring to FIG. 3, insertion tip 24 has a length 34, an outer radial dimension 36, and an inner radial dimension 38. Preferably, barrel 14 has a minimal thickness such that inner and outer dimensions 36, 38, respectively, can be considered to be substantially similar.

Length 34 is defined as the distance between first end 20 and plane 30. Insertion tip 24 is, preferably, tapered or elliptical in shape. Specifically, dimensions 36, 38 decrease along length 34, linearly or non-linearly, from a maximum at plane 30 to a minimum at first end 20.

The taper of insertion tip 24 is defined as a ratio of the maximum radial dimension of insertion tip 24, namely radial dimension 36 at plane 30, divided by length 34. Preferably, insertion tip 24 has a taper ratio of more than about 0.3 to less than 1.0, preferably about 0.6.

Figure 4:
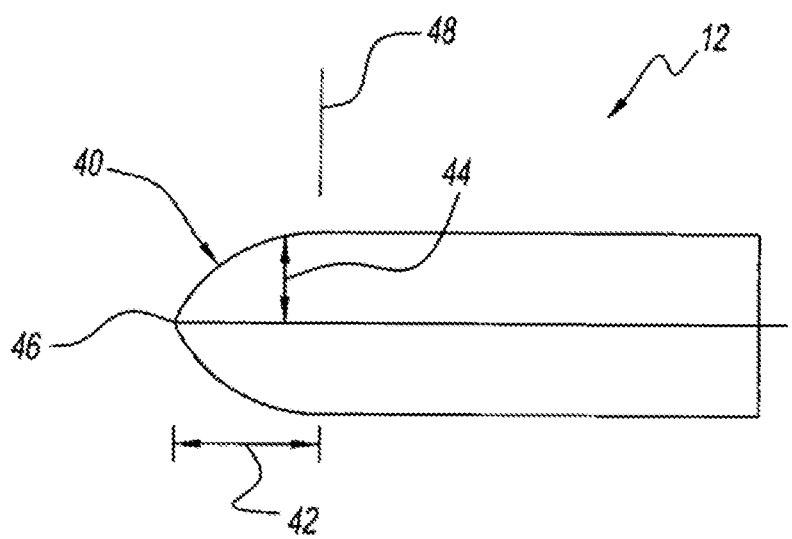
FIG. 4 is a side view of the shaped pledget of FIG. 1.

It has been determined that the perceived and actual level of comfort of assembly 10 can be enhanced through the use of shaped pledget 12, shown in FIG. 4, for supporting petals 26 of insertion tip 24.

Pledget 12 has a tip section 40 that is, preferably, shaped to support insertion tip 24. Tip section 40 has a length 42 and an outer radial dimension 44 that decreases or is tapered along length 42. Length 42 is defined as the distance between a front end 46 of pledget 12 and a plane 48. Plane 48 is defined as a plane through pledget 12 where the taper of tip section 40 begins.

Tip section 40 supports or contacts (hereinafter "supports") an inner surface area 50 of insertion tip 24 to provide increased comfort as compared to prior assemblies. Inner surface area 50 is defined as the surface area of tip 24 between first end 20 and plane 30.

Tip section 40 supports a portion 52 of inner surface area 50. Portion 52 is considered to be "supported" by tip section 40 when outer dimension 44 is at least about 75%, more preferably about 85%, most preferably about 95% of inner dimension 38.

Figure 5:
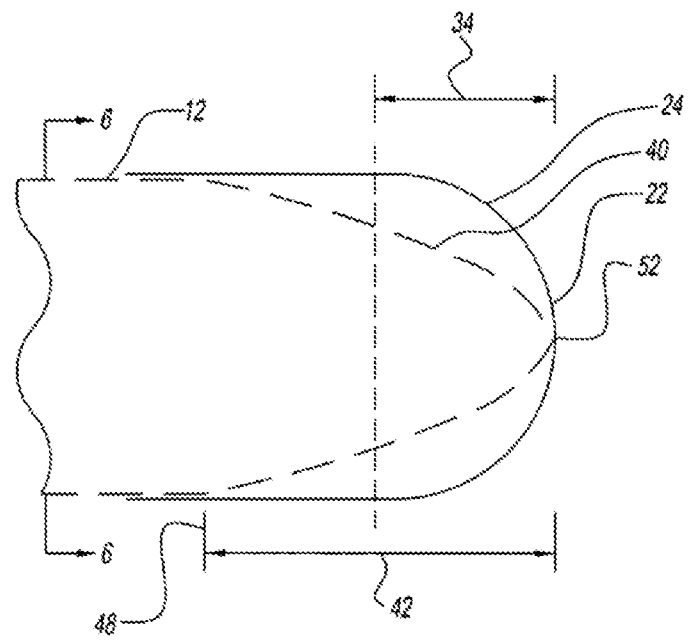
FIG. 5 is an exemplary embodiment of an insertion tip having a shaped pledget according to the present invention.
Figure 6:
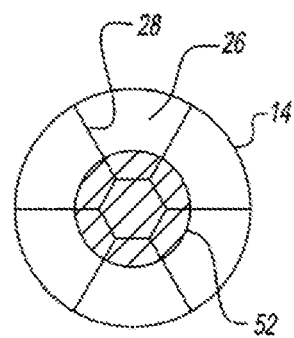
FIG. 6 is a view taken along lines 6-6 in FIG. 5.

Referring now to FIGS. 5 and 6, an exemplary embodiment of portion 52 supported by tip section 40 is illustrated. Insertion tip 24 is illustrated having a taper ratio of less than 1.0. Tip section 40 of pledget 12 is illustrated supporting portion 52, which starts at first end 20 and runs along in surface area 50 towards plane 30. In this embodiment, pledget 12 supports petals 26 at least at first end 20. It is contemplated that portion 52 can support at least about 10%, preferably at least about 50%, most preferably about 100% of surface area 50.

Figure 7:
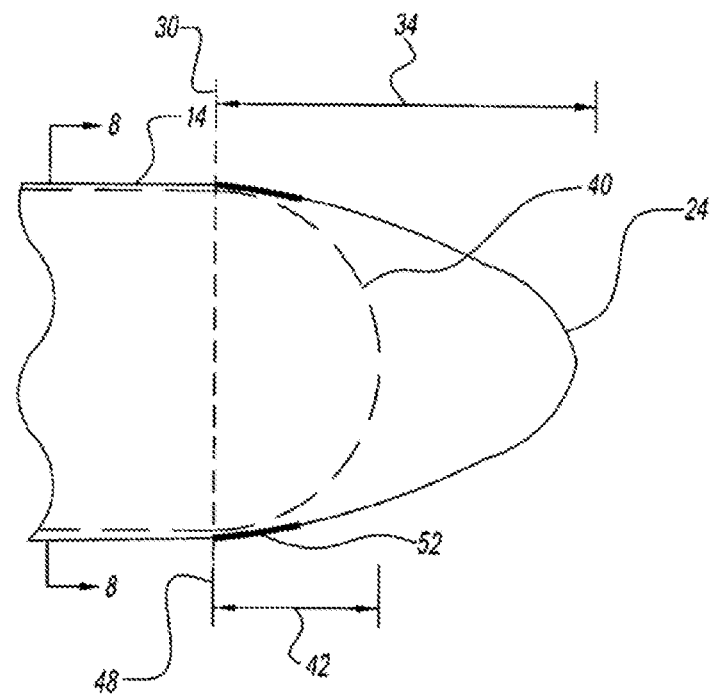
FIG. 7 is an alternate exemplary embodiment of an insertion tip having a shaped pledget.
Figure 8:
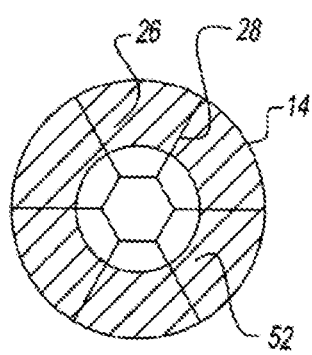
FIG. 8 is a view taken along lines 8-8 in FIG. 7.

Referring now to FIGS. 7 and 8, an alternate exemplary embodiment of portion 52 supported by tip section 40 is illustrated. Insertion tip 24 is illustrated having a taper ratio of about 0.7. Tip section 40 of pledget 12 is illustrated supporting portion 52, which starts at plane 30 and runs along inner surface area 50 towards first end 20. In this embodiment, pledget 12 supports petals 26 at least at the base of the petals, namely at least at plane 30. It is contemplated that portion 52 can support at least about 10%, preferably at least about 50%, most preferably about 100% of surface area 50.

Figure 9:
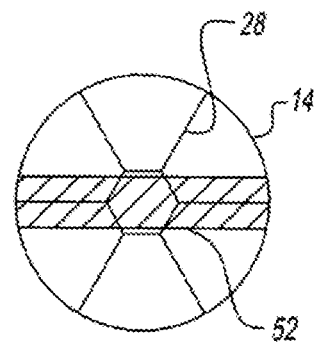
FIG. 9 is an alternate embodiment of the view of FIG. 8.

It should be recognized that portion 52 is illustrated in FIGS. 6 and 8 as being circular. However, it is also contemplated for tip section 40 of pledget 12 to support specific portions 52 of inner surface area 50. For example, portion 52 can support inner surface area 50 at least at slits 28 of petals 26 as illustrated in FIG. 9.

Shaped pledget 12 should, preferably, occupy at least about 50% of the volume of insertion tip 24, more preferably about 75%, most preferably about 95%, where the tip volume is the void defined by petals 26 and plane 30. When pledget 12 has a taper ratio (e.g., dimension 44 divided by dimension 42) that is greater than the taper ratio of insertion tip 24 as in FIG. 7, length 42 of pledget 12 should occupy at least about 50% of length 34 of insertion tip 24, more preferably about 75%, most preferably about 95%. However, when pledget 12 has a taper ratio that is less than the taper ratio of insertion tip 24 as in FIG. 5, dimension 44 of the pledget 12 at any given point along its length 42 should be at least about 50% of the dimension 38 of applicator tip 24 at the corresponding point, more preferably about 75%, most preferably about 95%. However, when pledget 12 has a taper ratio that is less than the taper ratio of insertion tip 23 as in FIG. 5, dimension 44 of the pledget at any given point along its length 42 should be at least about 50% of the dimension 38 of applicator tip 24 at the corresponding point, more preferably about 75%, most preferably about 95%.

Advantageously, shaped pledget 12 prevents forces on insertion tip 24 applied during insertion of barrel 14 into the body from collapsing petals 26 inward towards the pledget. Further, shaped pledget 12 enables the petals to be made thinner to decrease the expulsion force while stilling mitigating the collapse or deflection of petals 26.

Shaped pledget 12 also has been found to reduce instances of pinching and scratching by petals during insertion of barrel 14. In prior assemblies having blunt or unshaped pledgets, users often push the pledget as far into the applicator tip as possible prior to insertion of the applicator. However, this can cause the petals to open prematurely, namely before insertion of the barrel into the body. The open petals provide prior barrels with a "claw-like" insertion tip, which can scratch during insertion of the barrel. Also, the open petals can close during the insertion process, which can pinch the skin of the user. Since shaped pledget 12 supports surface area 50, assembly 10 mitigates instances of these drawbacks and deficiencies of prior assemblies having an unshaped pledget.

Assembly 10 has been found to increase comfort of use during both the insertion of barrel 14 and the expulsion of pledget 12. First, the taper ratio of insertion tip 24 facilitates insertion comfort by gradually parting the vulva-vaginal channel over a longer length of the barrel as compared to prior blunt ended barrels. In addition, tip section 40 of pledget 12 gradually opens petals 26 over a longer length of the pledget as compared to prior blunt ended pledgets.

Surprisingly, the applicator barrel having at most only three petals according to the present disclosure requires an ejection force to expel the shaped pledget from the barrel of less than about 50 ounces. In one embodiment, the ejection force required to expel the pledget from the barrel is between about 5 ounces to about 35 ounces. In another embodiment, the ejection force required to expel the shaped pledget from the barrel is between about 8 ounces to about 2.5 ounces.

The ejection force may be measured by any suitable procedure known in the art. By way of example, the ejection force may be measured as follows. A totally assembled tampon with post-formed petals is used in the test. A Weigh-Tronix™ scale (Model #WI-130 or equivalent) is used. The scale is tared. The weights are recorded in ounces. The applicator is grasped by the finger grip using the thumb and the middle finger. With the plunger end down, the applicator is placed on the top of the balance platform and a steady downward motion is applied until the pledget is ejected from the applicator barrel. The maximum ejection force indicated by the scale is recorded. Generally, the mean and standard deviation is determined for at least five samples.

Tip section 40 of pledget 12 can be shaped by compressing the tip to a higher density than the rest of the pledget. Alternately, tip section 40 can be shaped providing the tip with a less dense material that, when compressed, provides the tip with the same density as the rest of the pledget. In addition, tip section 40 of pledget 12 can be shaped by cutting or trimming the tip to the desired shape so that the tip has the same density as the rest of the pledget. Of course, combinations of one or more of the aforementioned methods is contemplated by the present invention.

Suitable materials for forming shaped pledget 12 include, for example, cellulosic fibers such as, but not limited to rayon fibers, cotton fibers, pulp fibers, and; superabsorbent, such as Oasis; absorbent foam, such as hydrophilic polyurethane foam; or any combinations thereof.

Suitable materials for forming barrel 14 and/or plunger 16 include, for example, biopolymer, cardboard, heat shrink plastic, paper slurry, plastic, plastic tubing, pulp slurry, pulp-molded paper, or any combinations thereof. By way of example, barrel 14 can be formed of low-density polyethylene (LDPE), and plunger 16 can be formed of axially oriented high-density polyethylene (HDPE).

It has also been discovered through consumer testing that consumers prefer a tampon assembly fabricated from a softer resin. Therefore, barrel 14 and/or plunger 16 may include a blend of about 0 wt. % to about 100 wt. % LDPE and about 100 wt. % to about 0 wt. % thermoplastic elastomer (TPE). In another preferred embodiment, barrel 14 and/or plunger 16 are formed from a blend comprising about 50% to about 90% LDPE, and about 50% to about 10% TPE. In another preferred embodiment, barrel 14 and/or plunger 16 are formed from a blend comprising about 80% LDPE and about 20% TPE.

In another embodiment according to the present disclosure, a preferred TPE to use is a tri-block (terpolymer), having an A-B-A configuration of monomers, in which monomer B is not the same as monomer A. Preferred monomer blocks are styrene, butadiene (or isoprene), and styrene. There are also other classes of thermoplastic elastomers that one could use. These include, for example, thermoplastic polyurethane elastomers and others. These and other classes are described in a book entitled Thermoplastic Elastomers: A Comprehensive Review, ed. N. R. Legge, G. Holden and H. E. Schroeder, Munich: Hauser, 1987, the disclosure of which is incorporated in its entirety by reference herein. Examples of other suitable resins that may be used in the present disclosure are described in co-owned U.S. Pat. Nos. 5,681,894; 5,986,000; 6,254,565; and 6,756,434, as well as related published Patent Application US2005/0070645 A1; the disclosures of which are incorporated in their entirety by reference herein.

Other additives could also be added to the polyolefins to provide specific benefits, such as greater thermal stability, greater flexibility, higher lubricity, anti-static behavior, greater latitude of processing, colorants, and so on. Such additives would be familiar to those skilled in the art of polymer and thermoplastic formulations. Examples are provided in standard texts, for example, Additives for Plastics, ed. J. Thuen, published by D.A.T.A. Inc. the International Plastics Selector, 1987. Another ext is the Plastics Compounding Redbook for Resin Producers, Formulators and Compounders, published annually by Advanstar Communications, Cleveland, Ohio, ed. La Verne Leonard.

It should be recognized that pledget 12, barrel 14, and/or plunger 16 can have any cross-sectional shape, such as circular and non-circular, including oval or polygonal shapes. Furthermore, it is contemplated by the present invention for the cross-sectional shape to vary along the length of pledget 12, barrel 14, and/or plunger 16.

It should also be noted that the terms "first", "second", and "third" and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the disclosure without departing from the scope thereof.

What is claimed is:

1. A tampon assembly comprising: a barrel comprised of a single layer tubular wall and having a first end and a second end, the barrel having a cylindrical section located between the first end and the second end and a plurality of discrete petals at the first end that define a tapered insertion tip section, the discrete petals being separated from each other by a plurality of cuts through the tubular wall, each of the plurality of cuts having a terminal end adjacent a base region of the plurality of discrete petals, the tapered insertion tip section extending a first length measured from the cylindrical section of the barrel to the first end of the barrel, the cylindrical section of the barrel being longer than the first length of the tapered insertion tip section, the tapered insertion tip section having a first taper ratio defined as a radius of the barrel at the base region divided by the first length of the tapered insertion tip section; a pledget located within the barrel, the pledget having a cylindrical portion that is located within the cylindrical section of the barrel, the pledget having an insertion end region that has been compressed to form a tapered pledget tip that has a tip density that is greater than an adjacent region density, the tapered pledget tip having an outer radial dimension that is at least about 75% of an inner radial dimension of the insertion tip section such that the tapered pledget tip supports a portion of an inner surface area of the plurality of the petals when the pledget tip is positioned adjacent the first end, the tapered pledget tip having a second taper ratio that is defined as a radius of the pledget at the cylindrical portion divided by a second length of the tapered pledget tip, the second taper ratio being greater than the first taper ratio, the tapered pledget tip fitting within the tapered insertion tip section and occupying at least about 50% of the first length of the tapered insertion tip section of the barrel; and a plunger slidably received in the second end of the barrel, the plunger moving through the cylindrical section of the barrel while expelling the pledget from the barrel.

2. The tampon assembly according to claim 1, wherein the first taper ratio is between about 0.3 and about 1.0.

3. The tampon assembly according to claim 2, wherein the first taper ratio is about 0.6.

4. The tampon assembly according to claim 1, wherein the tapered insertion tip section is generally elliptical in shape.

5. The tampon assembly according to claim 1, wherein the tapered pledget tip occupies at least about 85% of the volume of the tapered insertion tip section.

6. The tampon assembly according to claim 1, wherein the plunger is comprised of high-density polyethylene including a friction-reducing material.

7. The tampon assembly according to claim 1, wherein the tapered pledget tip occupies at least about 50% of a volume of the tapered insertion tip section.

8. A tampon assembly comprising: a barrel comprised of a single layer tubular wall and having a first end and a second end, the barrel having a cylindrical section located between the first end and the second end and a plurality of discrete petals at the first end that define a tapered insertion tip section, the discrete petals being separated from each other by a plurality of cuts through the tubular wall, each of the plurality of cuts having a terminal end adjacent a base region of the plurality of discrete petals, the tapered insertion tip section extending a first length measured from the cylindrical section of the barrel to the first end of the barrel, the cylindrical section of the barrel being longer than the first length of the tapered insertion tip section, the tapered insertion tip section having a first taper ratio defined as a radius of the barrel at the base region divided by the first length of the tapered insertion tip section; a pledget located within the barrel, the pledget having a cylindrical portion that is located within the cylindrical section of the barrel, the pledget having an insertion end region that has been compressed to form a tapered pledget tip that has a tip density that is the same as an adjacent region density, the tapered pledget tip having an outer radial dimension that is at least about 75% of an inner radial dimension of the insertion tip section such that the tapered pledget tip supports a portion of an inner surface area of the plurality of the petals when the pledget tip is positioned adjacent the first end, the tapered pledget tip having a second taper ratio that is defined as a radius of the pledget at the cylindrical portion divided by a second length of the tapered pledget tip, the second taper ratio being greater than the first taper ratio, the tapered pledget tip fitting within the tapered insertion tip section and occupying at least about 50% of the first length of the tapered insertion tip section of the barrel; and a plunger slidably received in the second end of the barrel, the plunger moving through the cylindrical section of the barrel while expelling the pledget from the barrel.

9. The tampon assembly according to claim 8, wherein the first taper ratio is between about 0.3 and about 1.0.

10. The tampon assembly according to claim 9, wherein the first taper ratio is about 0.6.

11. The tampon assembly according to claim 8, wherein the tapered insertion tip section is generally elliptical in shape.

12. The tampon assembly according to claim 8, wherein the tapered pledget tip occupies at least about 85% of the volume of the tapered insertion tip section.

13. The tampon assembly according to claim 8, wherein the plunger is comprised of high-density polyethylene including a friction-reducing material.

14. The tampon assembly according to claim 8, wherein the tapered pledget tip occupies at least about 50% of a volume of the tapered insertion tip section.

15. A tampon assembly comprising: a barrel comprised of a single layer tubular wall and having a first end and a second end, the barrel having a cylindrical section located between the first end and the second end and a plurality of discrete petals at the first end that define a tapered insertion tip section, the discrete petals being separated from each other by a plurality of cuts through the tubular wall, each of the plurality of cuts having a terminal end adjacent a base region of the plurality of discrete petals, the tapered insertion tip section extending a first length measured from the cylindrical section of the barrel to the first end of the barrel, the cylindrical section of the barrel being longer than the first length of the tapered insertion tip section, the tapered insertion tip section having a first taper ratio defined as a radius of the barrel at the base region divided by the first length of the tapered insertion tip section, the first taper ratio being between about 0.3 and about 1.0; the barrel being comprised of a low-density polyethylene including a friction-reducing material; a pledget located within the barrel, the pledget having a cylindrical portion that is located within the cylindrical section of the barrel, the pledget having an insertion end region that has been compressed to form a tapered pledget tip, the tapered pledget tip having an outer radial dimension that supports a portion of an inner surface area of the plurality of the petals when the pledget tip is positioned adjacent the first end, the tapered pledget tip having a second taper ratio that is defined as a radius of the pledget at the cylindrical portion divided by a second length of the tapered pledget tip, the second taper ratio being greater than the first taper ratio, the tapered pledget tip fitting within the tapered insertion tip section and occupying at least about 75% of the first length of the tapered insertion tip section of the barrel; and a plunger slidably received in the second end of the barrel and extending beyond a plurality of protrusions on the outer circumference of the tubular wall, the plunger moving through the cylindrical section of the barrel while expelling the pledget from the barrel.

16. The tampon assembly according to claim 15, wherein the first taper ratio is about 0.6.

17. The tampon assembly according to claim 15, wherein the tapered insertion tip section is generally elliptical in shape.

18. The tampon assembly according to claim 15, wherein the tapered pledget tip occupies at least about 75% of a volume of the tapered insertion tip section.

19. The tampon assembly according to claim 15, wherein the tapered pledget tip occupies at least about 95% of the first length of the tapered insertion tip section.

20. The tampon assembly according to claim 15, wherein the pledget is expelled from the barrel by an ejection force in the range of about 5 ounces to about 8 ounces.

* * * * *